United States Patent
Ohyama et al.

(10) Patent No.: US 6,949,259 B1
(45) Date of Patent: Sep. 27, 2005

(54) SOLID PREPARATIONS FOR ORAL USE

(75) Inventors: Toshinori Ohyama, Nogi-machi (JP); Masaru Imamizu, Nogi-machi (JP)

(73) Assignee: Kyorin Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 10/111,418

(22) PCT Filed: Nov. 10, 2000

(86) PCT No.: PCT/JP00/07905

§ 371 (c)(1),
(2), (4) Date: May 7, 2002

(87) PCT Pub. No.: WO01/34148

PCT Pub. Date: May 17, 2001

(30) Foreign Application Priority Data

Nov. 11, 1999 (JP) ................................ 11/320586

(51) Int. Cl.⁷ ............................ A61K 9/28; A61K 9/20
(52) U.S. Cl. .................. 424/474; 424/464; 424/465
(58) Field of Search ................ 424/464, 465, 424/474

(56) References Cited

U.S. PATENT DOCUMENTS 5,399,576 A * 3/1995 Missbach
6,031,004 A * 2/2000 Timmins et al.

FOREIGN PATENT DOCUMENTS

EP 846693 6/1998
EP 0 846 693 A1 * 10/1998
JP 11-255649 9/1999

* cited by examiner

Primary Examiner—Thurman K. Page
Assistant Examiner—Humera N. Sheikh
(74) Attorney, Agent, or Firm—Oblon, Spivak, McClelland, Maier & Neustadt, P.C.

(57) ABSTRACT

Solid preparations for oral use for facilitating the administration in a small dose of KRP-297, which is a ligand common to peroxisome proliferator-activated receptors PPAR α and PPAR γ (i.e., nuclear receptors) and has an effect of ameliorating insulin resistance, which contain the drug ingredient in a uniform content and can be easily and quantitatively taken. By preparing solid preparations for oral use composed of a trace amount of the drug ingredient together with pharmaceutical carriers, it is possible to provide tablets which contain the drug component in a uniform content and can be easily and quantitatively taken.

2 Claims, No Drawings

SOLID PREPARATIONS FOR ORAL USE

TECHNICAL FIELD

The present invention relates to solid preparations for oral use which contains a small amount of (±)-5-[(2,4-dioxothiazolidine-5-yl)methyl]-2-methoxy-N-[[4-(trifluoromethyl) phenyl]methyl] -benzamide (hereinafter abbreviated as KRP-297), and makes it possible to formulate powder of KRP-297 into an oral tablet capable of taking easily. KRP-297 is a common ligand against peroxisome proliferator-activated receptor γ (PPAR γ) concerning in the differentiation induction of adipocytes and PPAR a concerning in lipid-metabolism, among the isoforms of PPAR that is nuclear receptor, and has an improving action on the insulin resistance.

BACKGROUND TECHNOLOGIES

KRP-297 is a thiazolidine-2,4-dione derivative with novel structure (Japanese Unexamined Patent Publication No. Hei 9-48711) and has a potent blood glucose-lowering action and lipid-lowering action (Nomura M. et al, Bioorg. Med. Chem. Lett., 9 (1999), 533–538), which is now under clinical. No solid preparations for oral use that is uniform in the content of a small amount of active ingredient and capable of taking quantitatively and easily on clinical application of KRP-297 has been known.

The subject of the invention is to provide solid preparations for oral use that contains a small amount of active ingredient uniformly and is capable of taking quantitatively on clinical application of KRP-297.

DISCLOSURE OF THE INVENTION

The inventors have prepared solid preparations for oral use that contains a small amount of active ingredient uniformly and is capable of taking quantitatively on clinical application of KRP-297, leading to the completion of the invention. The inventive solid preparations for oral use is an oral solid preparations (tablet) with uniform content, prepared by formulating a small amount of KRP-297 with drug-making carriers (excipient, disintegrator, binder, lubricant and coating agent) and by granulating, pressing into tablet and coating.

The process for preparing the inventive pharmaceutical comprises the steps of mixing fine powdery KRP-297 with the excipient (for example, saccharides such as lactose and glucose, sugar alcohols such as D-sorbitol and mannitol, celluloses such as crystalline cellulose, starches such as corn starch, etc., preferably lactose and crystalline cellulose) and the disintegrator (for example, celluloses such as calcium carboxymethylcellulose, low substituted hydroxypropylcellulose, sodium cross carmelose and methylcellulose, cross povidone, partially pregelatinized starch, etc., preferably low substituted hydroxypropylcellulose), and further by adding the binder (for example, celluloses such as hydroxypropylcellulose, hydroxypropylmethylcellulose, ethylcellulose and methylcellulose, gelatin, polyvinyl alcohol, polyvinyl pyrrolidone, etc., preferably polyvinyl alcohol), followed by granulation. For the granulation, the fluidized bed granulator can be used well.

Following this, the lubricant (for example, magnesium stearate, calcium stearate, talc, hydrogenated oil, etc., preferably magnesium stearate) is added, the mixture is pressed into tablet, and further the coating agent (for example, celluloses such as hydroxypropylcellulose, hydroxypropylmethylcellulose, ethyl-cellulose and methylcellulose, hydroxypropylmethylcellulose phthalate, methacrylic acid copolymer, carnauba wax, etc., preferably hydroxypropylmethylcellulose and carnauba wax) is coated, thereby the oral solid preparations or tablet capable of taking more easily can be obtained.

In the tablet obtained in this way, 0.25 mg to 5 mg of KRP-297 can be contained uniformly as an active ingredient per tablet, and, by taking orally, the pharmaceutical can be taken quantitatively.

BEST EMBODIMENT TO PUT THE INVENTION INTO PRACTICE

In following, the invention will be illustrated based on the examples, but the invention is not confined to these examples.

EXAMPLE 1

Per tablet, 0.25 mg of KRP-297, 78.55 mg of lactose, 26.2 mg of crystalline cellulose and 12 mg of low substituted hydroxypropylcellulose were mixed. Then, using a fluidized bed granulator, an aqueous solution of 2.4 mg-equivalent polyvinyl alcohol was added thereto, and the mixture was granulated and dried. After screening and rectifying the granules, 0.6 mg of magnesium stearate were added and mixed, followed by pressing into tablet to obtain uncoated tablets. Onto the uncoated tablets thus obtained, 5 mg-equivalent hydroxypropylmethylcellulose 2910 were coated, and 0.001 mg of carnauba wax was added and mixed to obtain film-coated tablets.

EXAMPLE 2

Per tablet, 1 mg of KRP-297, 91.1 mg of lactose, 30.4 mg of crystalline cellulose and 14 mg of low substituted hydroxypropylcellulose were mixed. Then, using a fluidized bed granulator, an aqueous solution of 2.8 mg-equivalent polyvinyl alcohol was added thereto, and the mixture was granulated and dried. After screening and rectifying the granules, 0.7 mg of magnesium stearate were added and mixed, followed by pressing into tablet to obtain uncoated tablets. Onto the uncoated tablets thus obtained, 5 mg-equivalent hydroxypropylmethylcellulose 2910 were coated, and 0.001 mg of carnauba wax was added and mixed to obtain film-coated tablets.

EXAMPLE 3

Per tablet, 2.5 mg of KRP-297, 92 mg of lactose, 28 mg of crystalline cellulose and 14 mg of low substituted were mixed. Then, using a fluidized bed granulator, an aqueous solution of 2.8 mg-equivalent polyvinyl alcohol was added thereto, and the mixture was granulated and dried. After screening and rectifying the granules, 0.7 mg of magnesium stearate were added and mixed, followed by pressing into tablet to obtain uncoated tablets. Onto the uncoated tablets thus obtained, 5 mg-equivalent hydroxypropylmethylcellulose 2910 were coated, and 0.002 mg of carnauba wax were added and mixed to obtain film-coated tablets.

EXAMPLE 4

Per tablet, 5 mg of KRP-297, 103 mg of lactose, 32 mg of crystalline cellulose and 16 mg of low substituted hydroxypropylcellulose were mixed. Then, using a fluidized bed granulator, an aqueous solution of 3.2 mg-equivalent polyvinyl alcohol was added thereto, and the mixture was granulated and dried. After screening and rectifying the granules, 0.8 mg of magnesium stearate were added and mixed, followed by pressing into tablet to obtain uncoated tablets. Onto the uncoated tablets thus obtained, 5 mg-equivalent hydroxypropylmethylcellulose 2910 were coated, and then 0.002 mg of carnauba wax were added and mixed to obtain film-coated tablets.

EXAMPLE 5

Per tablet, 0.25 mg of KRP-297, 80.75 mg of lactose, 24 mg of crystalline cellulose and 12 mg of low substituted hydroxypropylcellulose were mixed. Then, using a fluidized bed granulator, an aqueous solution of 2.4 mg-equivalent polyvinyl alcohol was added thereto, and the mixture was granulated and dried. After screening and rectifying the granules, 0.6 mg of magnesium stearate were added and mixed, followed by pressing into tablet to obtain uncoated tablets. Onto the uncoated tablets thus obtained, 4 mg-equivalent hydroxypropylmethylcellulose 2910 were coated, and then 0.002 mg of carnauba wax were added and mixed to obtain film-coated tablets.

EXAMPLE 6

Per tablet, 1 mg of KRP-297, 93.5 mg of lactose, 28 mg of crystalline cellulose and 14 mg of low substituted hydroxypropylcellulose were mixed. Then, using a fluidized bed granulator, an aqueous solution of 2.8 mg-equivalent polyvinyl alcohol was added thereto, and the mixture was granulated and dried. After screening and rectifying the granules, 0.7 mg of magnesium stearate were added and mixed, followed by pressing into tablet to obtain uncoated tablets. Onto the uncoated tablets thus obtained, 5 mg-equivalent hydroxypropylmethylcellulose 2910 were coated, and 0.002 mg of carnauba wax were added and mixed to obtain film-coated tablets.

EXPERIMENTAL EXAMPLE

With the tablets obtained in respective examples, test was performed according to the uniformity test of content in the 13th revision Japanese Pharmacopoeia. As a result, uniform pharmaceuticals which meet the standard were obtained in all cases.

Results are shown in Table 1.

TABLE 1

Test results of uniformity of content of KRP-297 tablet

|  | Example 1 | Example 2 | Example 3 | Example 4 | Example 5 | Example 6 |
| --- | --- | --- | --- | --- | --- | --- |
| Av. value (%) | 98.4 | 100.9 | 99.9 | 99.8 | 100.4 | 100.1 |
| Range (%) | 96.8~102.9 | 100.2~101.5 | 98.7~100.9 | 98.6~101.1 | 99.4~100.7 | 99.1~101.1 |
| Judgment value (%) | 5.3 | 2.0 | 1.6 | 1.8 | 1.3 | 1.6 |

Judgment value: Value less than 15% conforts to the standard.

UTILIZABILITY IN THE INDUSTRY

According to the invention, an solid preparations for oral use of KRP-297, being a common ligand against PPAR α and PPAR γ and having an improving action on the insulin resistance, have been provided.

On clinical application of KRP-297, it was difficult to take quantitatively, if keeping it powdery as it is, because of a small amount of it. However, by mixing with drug-making carriers and by molding, the oral solid preparation that is uniform in the content of active ingredient and easy in the handling has been completed and it has become possible to take quantitatively and simply.

What is claimed is:

1. A solid preparation comprising 0.25 to 5 mg of (±)-5-[(2,4-dioxo-thiazolidine-5-yl)methyl]-2-methoxy-N-[[4-(trifluoromethyl)phenyl] -methyl]benzamide as an active ingredient and at least one carrier, wherein said solid preparation is suitable for oral administration and wherein (±)-5-[(2,4-dioxo-thiazolidine-5-yl)methyl]-2-methoxy-N-[[4-(trifluoromethyl)phenyl]-methyl]benzamide is uniformly contained in said solid preparation thereby making (±)-5-[(2,4-dioxo-thiazolidine-5-yl)methyl]-2-methoxy-N-[[4-(trifluoromethyl)phenyl]-methyl]benzamide easy to orally administer, wherein the solid preparation is prepared by mixing 0.25 to 5 mg of (±)-5-[(2,4-dioxo-thiazolidine-5-yl)methyl]-2-methoxy-N-[[4-(trifluoromethyl)phenyl] -methyl]benzamide, lactose, crystalline cellulose, and low substituted hydroxypropylcellulose to obtain a mixture;

granulating with drying in the presence of an aqueous solution of polyvinyl alcohol with a fluidized bed granulator to obtain a granulated product; then mixing the granulated product with magnesium stearate after screening and rectifying the granules from the granulator to obtain a second mixture; and pressing the second mixture into a tablet.

2. The solid preparation of claim 1, wherein after the tablet is formed, the tablet is coated to form a coated tablet.

* * * * *